United States Patent
Rosti et al.

(10) Patent No.: US 10,117,781 B2
(45) Date of Patent: Nov. 6, 2018

(54) EAR CUP FOR A HEARING PROTECTOR

(71) Applicant: SAVOX COMMUNICATIONS OY AB (LTD), Espoo (FI)

(72) Inventors: Janne Rosti, Luhtajoki (FI); Ville Riikonen, Veikkola (FI)

(73) Assignee: SAVOX COMMUNICATIONS OY AB (LTD)., Espoo (FI)

(*) Notice: Subject to any disclaimer, the term of this patent is extended or adjusted under 35 U.S.C. 154(b) by 0 days.

(21) Appl. No.: 15/517,552

(22) PCT Filed: Oct. 1, 2015

(86) PCT No.: PCT/FI2015/050649
§ 371 (c)(1),
(2) Date: Apr. 7, 2017

(87) PCT Pub. No.: WO2016/055693
PCT Pub. Date: Apr. 14, 2016

(65) Prior Publication Data
US 2017/0304121 A1    Oct. 26, 2017

(30) Foreign Application Priority Data
Oct. 7, 2014 (FI) .................................. 20145881

(51) Int. Cl.
*H04R 1/10* (2006.01)
*A61F 11/14* (2006.01)
(Continued)

(52) U.S. Cl.
CPC .......... *A61F 11/14* (2013.01); *G10L 21/0232* (2013.01); *H04R 1/1008* (2013.01);
(Continued)

(58) Field of Classification Search
CPC ...... H04R 1/1008; H04R 1/1041; H04R 3/04; H04R 19/04; H04R 2201/003; H04R 1/10;
(Continued)

(56) References Cited

U.S. PATENT DOCUMENTS 3,683,130 A * 8/1972 Kahn ................... H04R 1/1041
                                                                  379/392
5,438,698 A * 8/1995 Burton .................. H01Q 1/276
                                                                  2/209.13
(Continued)

FOREIGN PATENT DOCUMENTS

CN    201146592 Y    11/2008
EP    1 453 213 A2    9/2004
WO    2008/122081 A1    10/2008

OTHER PUBLICATIONS

International Search Report, dated Dec. 18, 2015, from corresponding PCT application.
(Continued)

*Primary Examiner* — Jason R Kurr
(74) *Attorney, Agent, or Firm* — Young & Thompson

(57) ABSTRACT

An ear cup for a hearing protector includes a cup-shaped outer casing, a sealing ring on a rim of the outer casing, and at least one electrical component such as a microphone. The electrical component is mounted on a flexible circuit board attached on the outer surface of the outer casing, where the outer casing includes a slit through which the flexible circuit board extends to the inside of the outer casing so as to provide electrical connections between the electrical component and an electrical circuitry inside the outer casing. Thus, there is no need for wide openings on the outer casing of the ear cup, instead only a narrow slit suffices. This facilitates achieving good noise reduction properties.

18 Claims, 3 Drawing Sheets

(51) Int. Cl.
    *H04R 3/04*      (2006.01)
    *H04R 19/04*     (2006.01)
    *G10L 21/0232*   (2013.01)

(52) U.S. Cl.
    CPC ............ *H04R 1/1041* (2013.01); *H04R 3/04* (2013.01); *H04R 19/04* (2013.01); *A61F 2011/145* (2013.01); *H04R 2201/003* (2013.01)

(58) Field of Classification Search
    CPC . H04R 1/1066; H04R 1/1075; G10L 21/0232; A61F 11/14; A61F 2011/145
    See application file for complete search history.

(56) References Cited

U.S. PATENT DOCUMENTS

| | | | |
|---|---|---|---|
| 9,049,502 B2 * | 6/2015 | Pelland | ............... H04M 1/0254 |
| 2002/0080987 A1 | 6/2002 | Almqvist | |
| 2009/0290743 A1 | 11/2009 | Carroll | |
| 2014/0259287 A1 | 9/2014 | Waters et al. | |

OTHER PUBLICATIONS

FI Search Report, dated Apr. 9, 2015, from corresponding FI application.

* cited by examiner

EAR CUP FOR A HEARING PROTECTOR

FIELD OF THE INVENTION

The invention relates to an ear cup for a hearing protector, where the ear cup is provided with at least one electrical component which may comprise, for example but not necessarily, a microphone. Furthermore, the invention relates to a hearing protector.

BACKGROUND

In many cases there is a need to provide an ear cup of a hearing protector with one or more electrical components which may comprise for example a microphone for receiving voice from outside of the ear cup and for converting the voice into an audio electrical signal. The ear cup may further comprise a signal processing system for processing the audio electrical signal. The signal processing system may comprise for example a filter for filtering the audio electrical signal and an earphone for procuring voice corresponding to the filtered audio electrical signal. The filter can be adapted to attenuate impulse noise and/or to attenuate signal components which do not belong to a desired frequency band, e.g. to the frequency band of speech.

Design of the ear cups of a hearing protector is critical for outside noise attenuation. Any holes or openings on the outer casing of an ear cup cause noise to leak inside and thus the holes or openings deteriorate significantly the noise reduction properties of the ear cup. In addition, any hard material that occupies a portion of the internal volume of the ear cup deteriorates also the noise attenuation properties because the room for soft noise-damping material is diminished.

A microphone and user interface devices, such as e.g. push buttons, are typically mounted mainly inside an ear cup and have large openings in the outer casing of the ear cup. For example, a classical cylindrical electret condenser microphone is typically mounted to a wide opening of the outer casing with the aid of a rubber mounting and sealing element. Therefore, the traditional way to provide an ear cup of a hearing protector with a microphone and with user interface devices deteriorates the noise reduction properties.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the invention, there is provided a new ear cup for a hearing protector. An ear cup according to the invention comprises:
- an outer casing,
- a sealing ring on the rim of the outer casing and suitable for sealingly abut against the head of a user around an ear of the user, and
- at least one electrical component, for example a microphone, outside the outer casing.

The at least one electrical component is mounted on a flexible circuit board attached on an outer surface of the outer casing, where the outer casing comprises a slit through which the flexible circuit board extends to inside of the outer casing so as to provide electrical connections between the electrical component and an electrical circuitry inside the outer casing.

In the above-described ear cup, there is no need for wide openings on the outer casing of the ear cup, instead only a narrow slit suffices. Acoustical sealing of the narrow slit is easier than acoustical sealing of wide openings. Therefore, the noise reduction properties of the above-described ear cup can be better than e.g. in a case where a classical cylindrical electret condenser microphone is mounted to a wide opening of an ear cup with the aid of a rubber mounting element.

In cases where the at least one electrical component comprises a microphone, it is straightforward to use a Micro Electro Mechanical Systems "MEMS" microphone because the MEMS microphone is mounted on the flexible circuit board and, on the other hand, typical MEMS microphones are intended for printed circuit board "PCB" mounting. For traditional ear cup designs, the MEMS microphones are often cumbersome because, as mentioned above, typical MEMS microphones are intended for printed circuit board mounting.

In accordance with the invention, there is provided also new hearing protector that comprises two ear cups and a band for mechanically interconnecting the ear cups. At least the one of the ear cups is an ear cup according to the invention. The hearing protector may comprise an electrical cable for transferring one or more electrical signals between the ear cups.

A number of exemplifying and non-limiting embodiments of the invention are described in accompanied dependent claims.

Various exemplifying and non-limiting embodiments of the invention both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of also un-recited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

Exemplifying embodiments of the invention and their advantages are explained in greater detail below in the sense of examples and with reference to the accompanying drawings, in which.

DESCRIPTION OF EXEMPLIFYING AND NON-LIMITING EMBODIMENTS

Figure 1A:
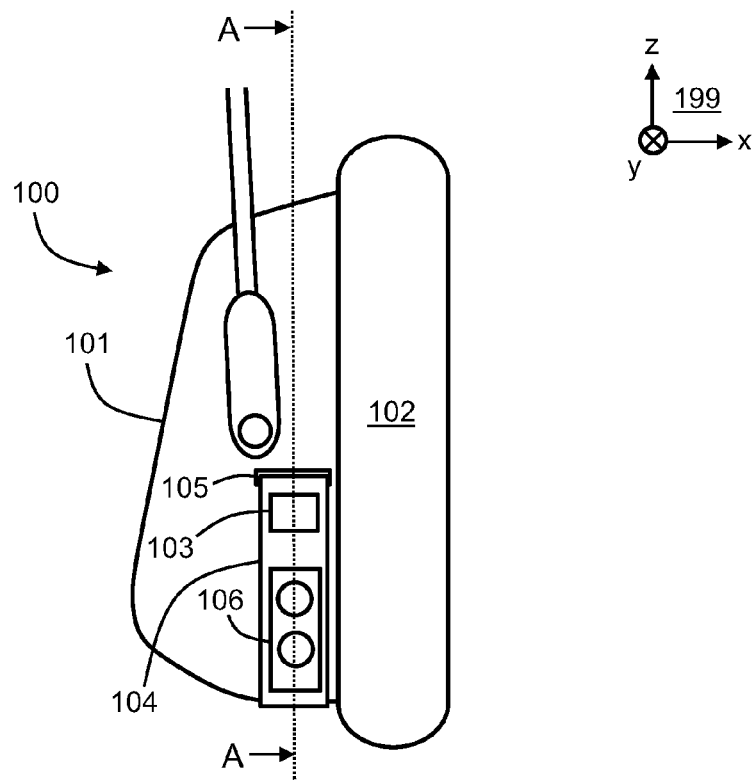
FIGS. 1a and 1b illustrate an ear cup according to an exemplifying and non-limiting embodiment of the invention.
Figure 1B:
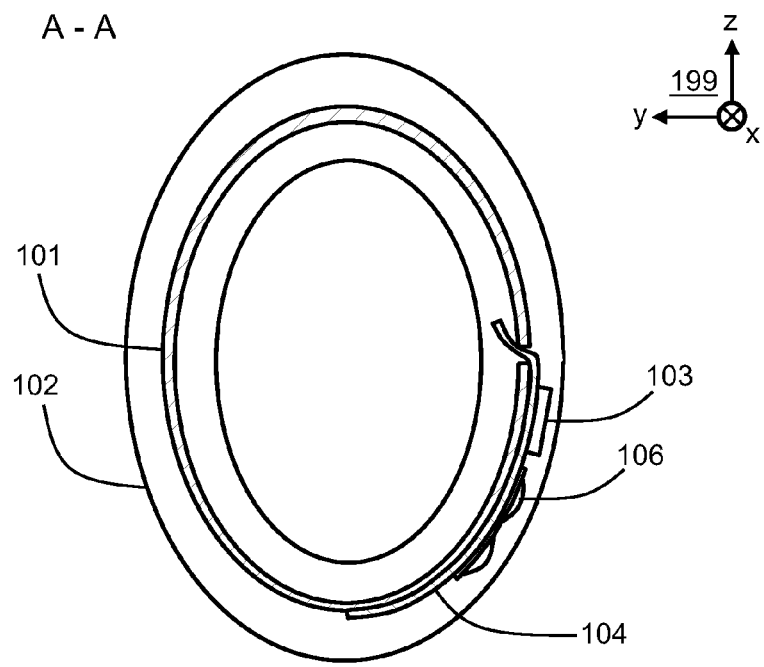

FIG. 1a shows a side view of an ear cup 100 according to an exemplifying and non-limiting embodiment of the invention. FIG. 1b shows a view of a section taken along a line A-A shown in FIG. 1a. The section plane is parallel with the yz-plane of a coordinate system 199. The ear cup comprises an outer casing 101 and a sealing ring 102 on the rim of the outer casing and suitable for sealingly abut against the head of a user around an ear of the user. The ear cup further comprises a flexible circuit board 104 attached on the outer surface of the outer casing 101. Furthermore, the ear cup comprises electrical components 103 and 106 mounted on the flexible circuit board. The outer casing 101 of the ear cup comprises a slit 105 through which the flexible circuit board 104 extends to inside of the outer casing as illustrated in FIG. 1b. The part of the flexible circuit board 104 which extends to the inside of the outer casing 101 provides electrical connections between the electrical components 103 and 106 and an electrical circuitry inside the outer casing 101.

In the exemplifying and non-limiting case illustrated in FIGS. 1a and 1b, the electrical component 103 is a microphone and the electrical component 106 comprises user interface devices for enabling the user to control the operation of the ear cup. The user interface devices may comprise for example push buttons. The microphone is advantageously a Micro Electro Mechanical Systems "MEMS" microphone because MEMS microphones have several advantages with respect to e.g. classical electret microphones. For example, immunity to electrical interferences is superior to that of a classical electret microphone when using a digital MEMS microphone with an integrated analog-to-digital conversion. Also the variation of performance is very small with MEMS microphones, and the environmental and mechanical endurance is typically better than that of traditional microphone structures. Furthermore, MEMS microphones are small and have advantageous acoustical properties for active hearing protection since the MEMS microphones have low noise and high sensitivity. Yet furthermore, many MEMS microphones are suitable for automated printed circuit board "PCB" mounting.

The above-presented structure, where the flexible circuit board 104 is attached on the outer surface of the outer casing 101 and the electrical components are mounted on the flexible circuit board 104, makes it possible that the amount of the electrical components, e.g. push buttons and microphones, has practically no effect on the size of the slit 105. Furthermore, the interior of the outer casing 101 has more room for soft noise-damping material than in a traditional design where the outer casing has individual openings for a microphone and for each push button and where the microphone and the push buttons are partly in the interior of the outer casing.

It is worth noting that the above-presented principle of providing an ear cup of a hearing protector with one or more electrical components is not limited to cases where at least one of the electrical components is a microphone. For example, in an ear cup according to another exemplifying and non-limiting embodiment of the invention, the electrical component 103 can be for example a radio frequency identifier "RFID" tag.

Figure 2:
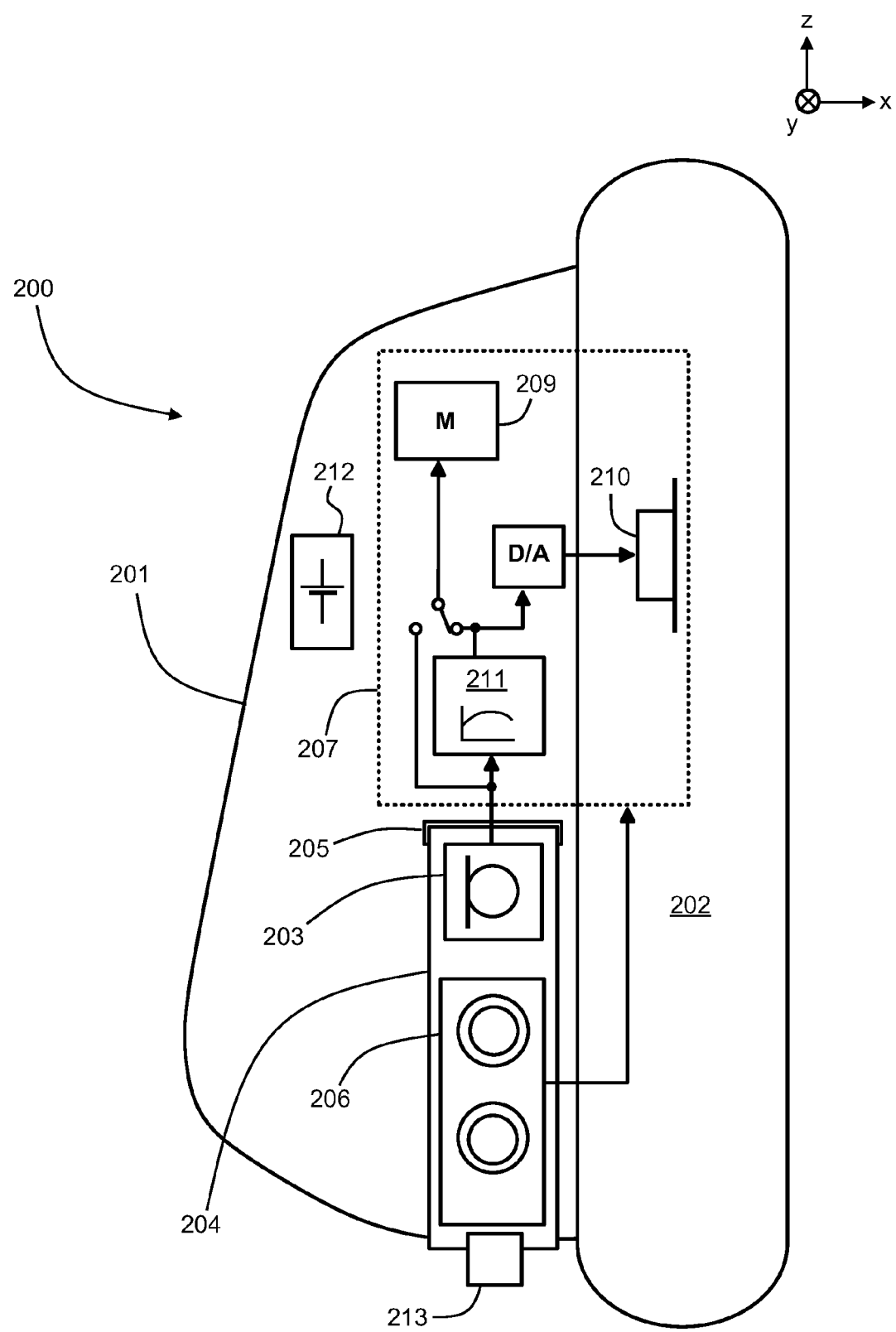
FIG. 2 shows a functional block diagram of an ear cup according to an exemplifying and non-limiting embodiment of the invention.

FIG. 2 shows a functional block diagram of an ear cup 200 according to an exemplifying and non-limiting embodiment of the invention. The ear cup comprises an outer casing 201 and a sealing ring 202 on the rim of the outer casing and suitable for sealingly abut against the head of a user around an ear of the user. The ear cup further comprises a flexible circuit board 204 attached on the outer surface of the outer casing 201. Furthermore, the ear cup comprises electrical components 203 and 206 mounted on the flexible circuit board. The outer casing 201 of the ear cup comprises a slit 205 through which the flexible circuit board 204 extends to inside of the outer casing. The part of the flexible circuit board 204 which extends to the inside of the outer casing 201 provides electrical connections between the electrical components 203 and 206 and a signal processing system 207 inside the outer casing 201.

In the exemplifying and non-limiting case illustrated in FIG. 2, the electrical component 203 is a microphone for receiving voice from outside of the ear cup and for converting the voice into an audio electrical signal. The microphone 203 is provided with an integrated analog-to-digital conversion so as to produce the audio electrical signal in a digital form. The microphone is advantageously a digital Micro Electro Mechanical Systems "MEMS" microphone.

In an ear cup according to an exemplifying and non-limiting embodiment of the invention, the signal processing system 207 comprises a memory 209 for storing the audio electrical signal in the digital form.

In an ear cup according to an exemplifying and non-limiting embodiment of the invention, the signal processing system 207 comprises a filter 211 for filtering the audio electrical signal. The filter 211 can be implemented for example with a digital signal processor "DSP". The filter 211 can be adapted to attenuate impulse noise from the audio electrical signal and/or to attenuate such portions of the audio electrical signal which are outside a pre-determined frequency band. The pre-determined frequency band can be for example the phone band from about 300 Hz to about 3 kHz.

In an ear cup according to an exemplifying and non-limiting embodiment of the invention, the signal processing system 207 comprises an earphone 210 for producing voice corresponding to the filtered audio electrical signal.

In an ear cup according to an exemplifying and non-limiting embodiment of the invention, the electrical component 206 comprises one or more user interface devices, e.g. push buttons, for enabling the user to control the operation of the ear cup.

An ear cup according to an exemplifying and non-limiting embodiment of the invention comprises a battery 212 and/or a super capacitor for energizing the electrical components 203 and 206 and the signal processing system 207. The ear cup may further comprise an electrical connector 213 mounted on the flexible circuit board 204 and suitable for receiving and transmitting electrical signals from and to external devices and/or for receiving electrical power for charging the battery 212 and/or the super capacitor. It is also possible that the ear cup does not comprise a battery or a super capacitor, but the ear cup is connected with an electrical cable to an external power source carried by the user.

Figure 3:
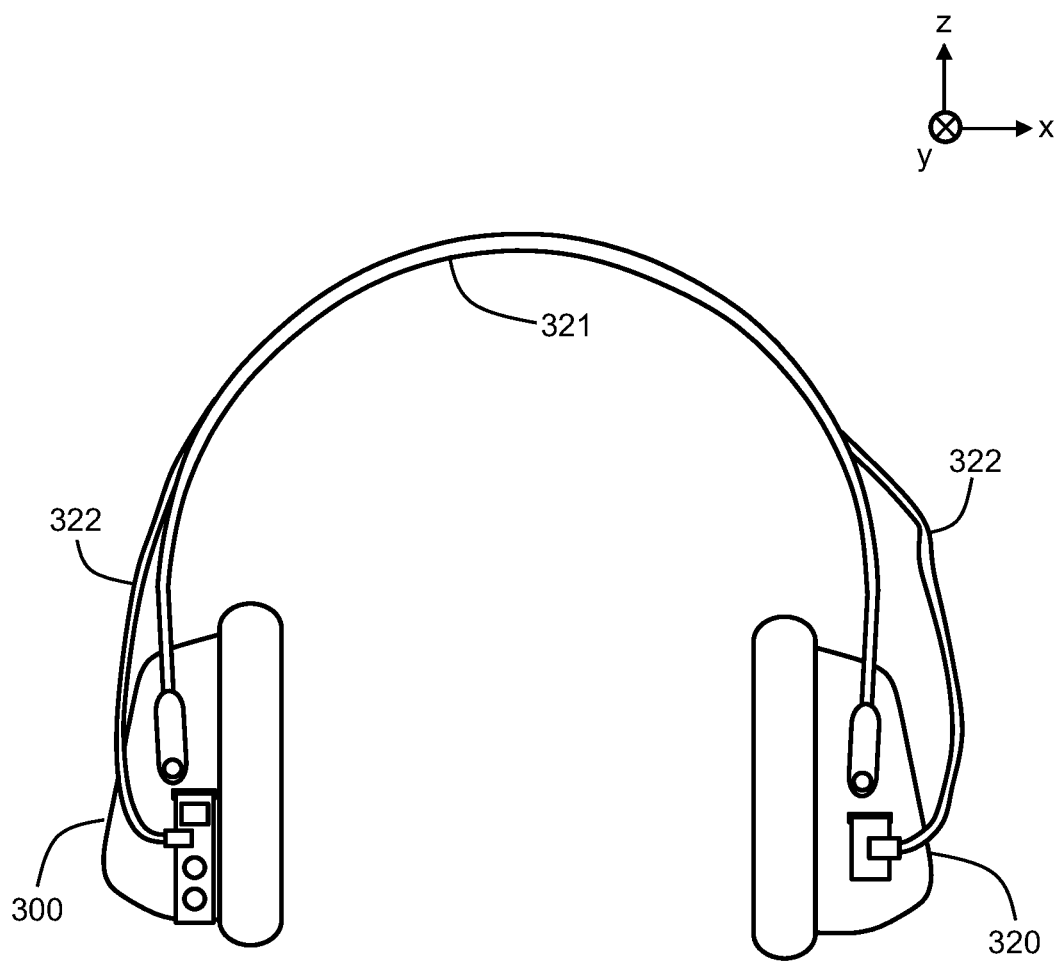
FIG. 3 shows a hearing protector according to an exemplifying and non-limiting embodiment of the invention.

FIG. 3 shows a hearing protector according to an exemplifying and non-limiting embodiment of the invention. The hearing protector comprises a first ear cup 300, a second ear cup 320, and a band 321 for mechanically interconnecting the first and second ear cups. At least one of the first and second ear cups is an ear cup according to an embodiment of the invention, e.g. such as illustrated in FIG. 2. The hearing protector may further comprise an electrical cable 322 for transferring one or more electrical signals between the first and second ear cups 300 and 320.

The specific examples provided in the description given above should not be construed as limiting. Therefore, the invention is not limited merely to the embodiments described above. For example, the signal processing system 207 illustrated in FIG. 2 is merely an example and various different signal processing systems digital, analog, and partly digital-partly analog are possible.

What is claimed is:

1. An ear cup for a hearing protector, the ear cup comprising:
an outer casing,
a sealing ring on a rim of the outer casing and suitable for sealingly abut against a head of a user around an ear of the user, and
at least one electrical component outside the outer casing, wherein the electrical component is mounted on a flexible circuit board attached on an outer surface of the outer casing, the outer casing comprising a slit through which the flexible circuit board extends to inside of the outer casing so as to provide electrical connections between the electrical component and an electrical circuitry inside the outer casing.

2. An ear cup according to claim 1, wherein the at least one electrical component comprises a microphone for receiving voice from outside of the ear cup and for converting the voice into an audio electrical signal.

3. An ear cup according to claim 2, wherein the microphone is a micro-electro-mechanical system microphone.

4. An ear cup according to claim 3, wherein the electrical circuitry comprises a signal processing system for processing the audio electrical signal.

5. An ear cup according to claim 2, wherein the microphone comprises an analog-to-digital converter so as to produce the audio electrical signal in a digital form.

6. An ear cup according to claim 5, wherein the electrical circuitry comprises a signal processing system for processing the audio electrical signal.

7. An ear cup according to claim 2, wherein the electrical circuitry comprises a signal processing system for processing the audio electrical signal.

8. An ear cup according to claim 7, wherein the signal processing system comprises a memory for storing the audio electrical signal.

9. An ear cup according to claim 7, wherein the signal processing system comprises a filter for filtering the audio electrical signal.

10. An ear cup according to claim 9, wherein the filter is adapted to attenuate at least one of the following: impulse noise, a portion of the audio electrical signal outside a pre-determined frequency band.

11. An ear cup according to claim 10, wherein the signal processing system comprises an earphone for producing voice corresponding to the filtered audio electrical signal.

12. An ear cup according to claim 9, wherein the signal processing system comprises an earphone for producing voice corresponding to the filtered audio electrical signal.

13. An ear cup according to claim 2, wherein the microphone comprises an analog-to-digital converter so as to produce the audio electrical signal in a digital form.

14. An ear cup according to claim 13, wherein the electrical circuitry comprises a signal processing system for processing the audio electrical signal.

15. An ear cup according to claim 14, wherein the signal processing system comprises a filter for filtering the audio electrical signal.

16. An ear cup according to claim 1, wherein the at least one electrical component comprises one or more user interface devices for enabling the user to control operation of the ear cup.

17. A hearing protector comprising a first ear cup, a second ear cup, and a band for mechanically interconnecting the first and second ear cups, wherein at least the first ear cup comprises:
an outer casing,
a sealing ring on a rim of the outer casing and suitable for sealingly abut against a head of a user around an ear of the user, and
at least one electrical component outside the outer casing, wherein the electrical component is mounted on a flexible circuit board attached on an outer surface of the outer casing, the outer casing comprising a slit through which the flexible circuit board extends to inside of the outer casing so as to provide electrical connections between the electrical component and an electrical circuitry inside the outer casing.

18. A hearing protector according to claim 17, wherein the hearing protector comprises an electrical cable for transferring one or more electrical signals between the first ear cup and the second ear cup.

* * * * *